(12) United States Patent
Holsinger

(10) Patent No.: US 6,193,729 B1
(45) Date of Patent: *Feb. 27, 2001

(54) SURGICAL COMBINATION APPARATUS HAVING FIRST AND SECOND INSTRUMENTS OPERATED FROM A COMMON ACTUATOR

(75) Inventor: Damond Holsinger, Midvale, UT (US)

(73) Assignee: Ballard Medical Products, Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/351,593

(22) Filed: Jul. 12, 1999

Related U.S. Application Data

(63) Continuation of application No. 08/633,958, filed on Apr. 15, 1996, now Pat. No. 5,947,978.

(51) Int. Cl.⁷ .................................................. A61B 17/26
(52) U.S. Cl. ..................... 606/113; 606/110; 600/564; 600/567
(58) Field of Search .................................. 606/110, 112, 606/113, 114, 127, 185, 1; 604/164, 205–210; 600/562, 563, 564, 565, 566, 567, 104, 106

(56) References Cited

U.S. PATENT DOCUMENTS

| | | | |
|---|---|---|---|
| 2,162,681 | * 6/1939 | Ryan | 606/104 |
| 2,856,933 | * 10/1958 | Hildebrand et al. | 606/113 |
| 4,085,743 | * 4/1978 | Yoon | 606/206 |
| 4,222,380 | * 9/1980 | Terayama | 604/164 |
| 4,592,341 | 6/1986 | Omagari et al. | |
| 4,598,699 | * 7/1986 | Garren et al. | 606/185 |
| 4,807,626 | 2/1989 | McGirr | |
| 4,815,476 | 3/1989 | Clossick | |
| 4,832,023 | 5/1989 | Murphy-Chutorian et al. | |
| 5,026,366 | 6/1991 | Leckrone | |
| 5,026,377 | 6/1991 | Burton et al. | |
| 5,084,054 | 1/1992 | Bencini et al. | |
| 5,163,942 | 11/1992 | Rydell | |
| 5,176,688 | * 1/1993 | Narayan et al. | 606/185 |

(List continued on next page.)

OTHER PUBLICATIONS

Copy of Ballard Medical Products' Hospital Price List for Endoscopic Accessories, prices effective Mar. 15, 1995.

Copy of Cox Medical Enterprises, Inc.'s 510(k) Premarket Notification for the Cox "Modular" Biopsy Forcep Autoclavable Handle/Cable/Fork/Cups with Attachable Disposable Catheter, dated Dec. 14, 1994.

Copy of Olympus Endoscopy Products Price List, effective Mar. 1, 1991.

*Primary Examiner*—Pedro Philogene
(74) *Attorney, Agent, or Firm*—Dority & Manning

(57) ABSTRACT

A surgical apparatus is provided having a first instrument and a second instrument which are independently operable, but may be used in tandem. The first instrument may comprise a needle and the second instrument may comprise a snare for cutting, excising, or trapping tissue. An actuator extends the needle a fixed first length relative to a distal end of the catheter for independently extending or retracting the second instrument a variable second length relative to the catheter distal end. The needle may be biased to retract relative to the distal end of the catheter. The actuator has a support and a slider. The slider is connected to the support for movement in opposite directions relative the support to allow freedom of action. The first instrument is secured to the support and rail, and the second instrument is secured to the slider. A rail enables independent but non-simultaneous sliding movement of the first instrument, or needle, while the slider facilitates independent operation of the second instrument, or snare.

15 Claims, 7 Drawing Sheets

U.S. PATENT DOCUMENTS

| | | |
|---|---|---|
| 5,190,542 | 3/1993 | Nakao et al. . |
| 5,241,970 | 9/1993 | Johlin, Jr. et al. . |
| 5,290,294 | 3/1994 | Cox et al. . |
| 5,290,299 | 3/1994 | Fain et al. . |
| 5,334,143 | 8/1994 | Carroll . |
| 5,336,227 | 8/1994 | Nakao et al. . |
| 5,376,094 | 12/1994 | Kline . |
| 5,395,367 | 3/1995 | Wilk . |
| 5,437,659 | 8/1995 | Leckrone . |
| 5,456,694 | 10/1995 | Marin et al. . |
| 5,542,948 * | 8/1996 | Weaver et al. ............... 606/110 |
| 5,653,716 * | 8/1997 | Malo et al. ................... 606/110 |
| 5,683,413 | 11/1997 | Miyagi . |
| 5,921,915 | 7/1999 | Aznoian et al. . |
| 5,931,849 | 8/1999 | Desvignes et al. . |
| 5,947,978 * | 9/1999 | Holsinger ..................... 606/110 |

\* cited by examiner

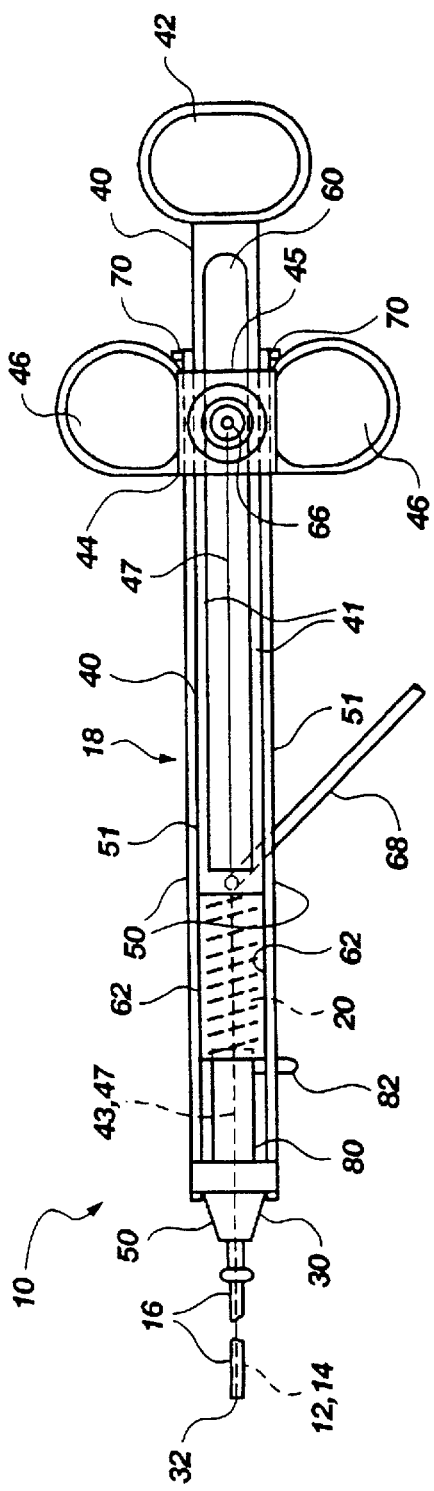
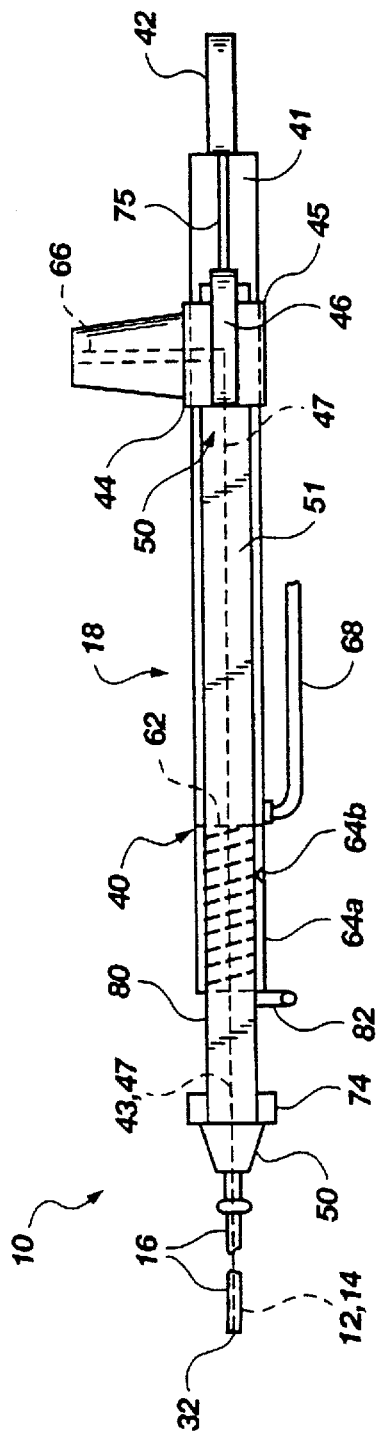
Fig. 1
Fig. 2

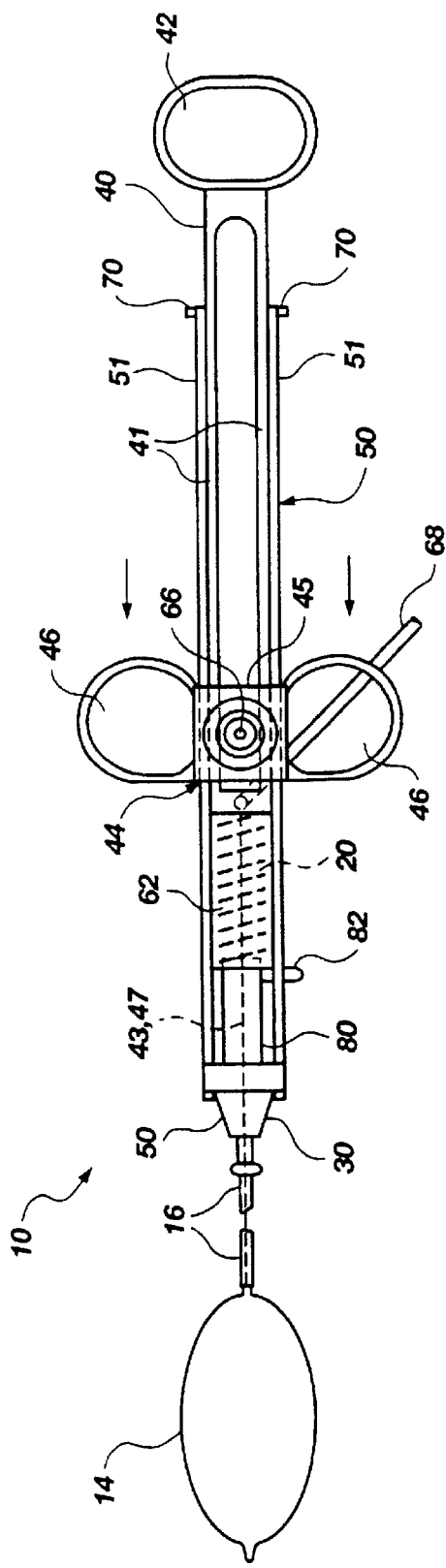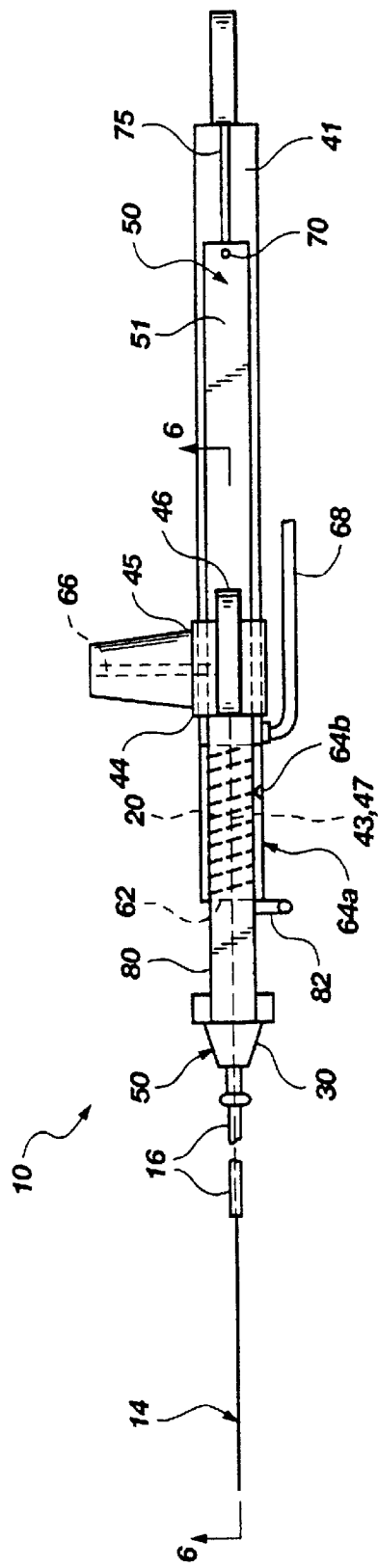

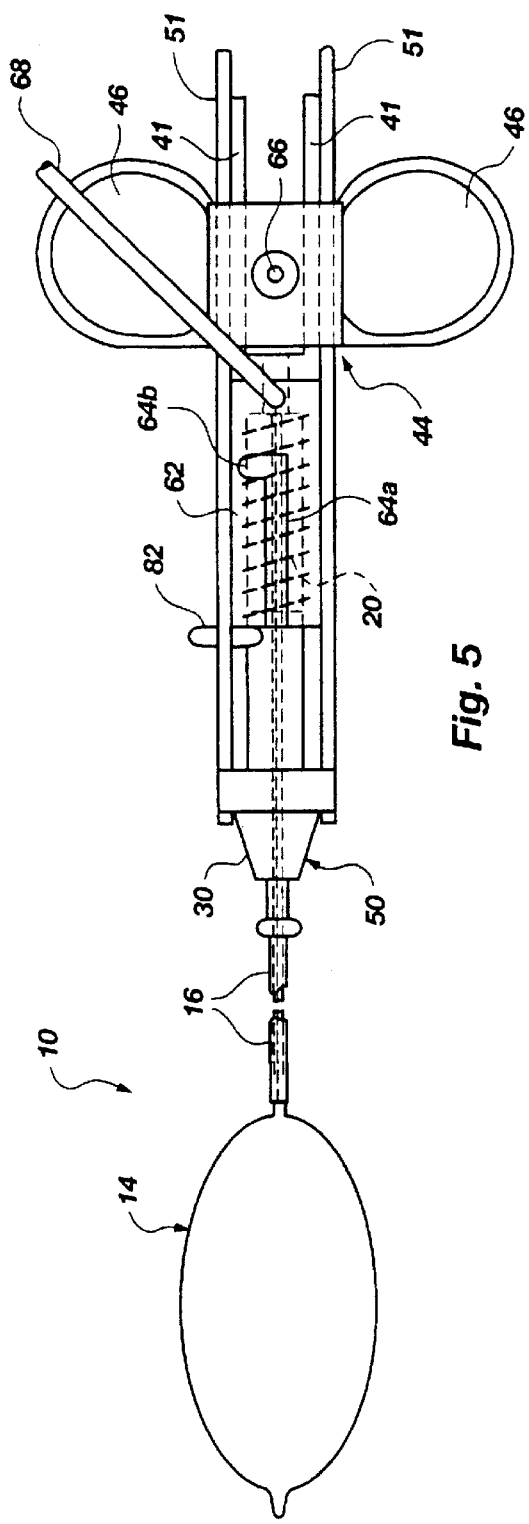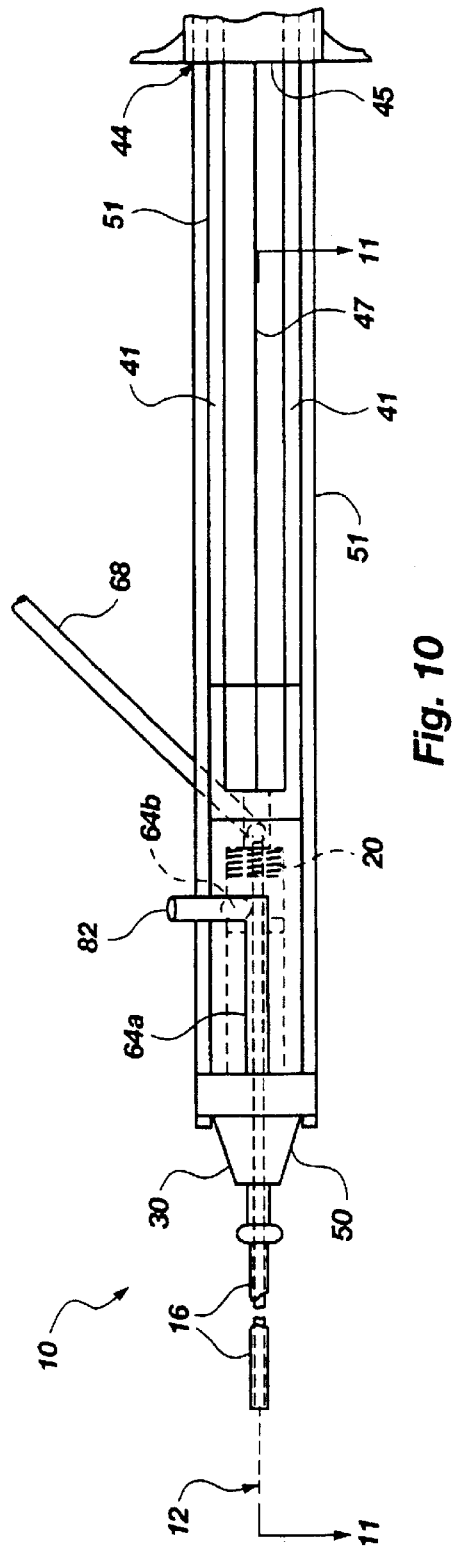

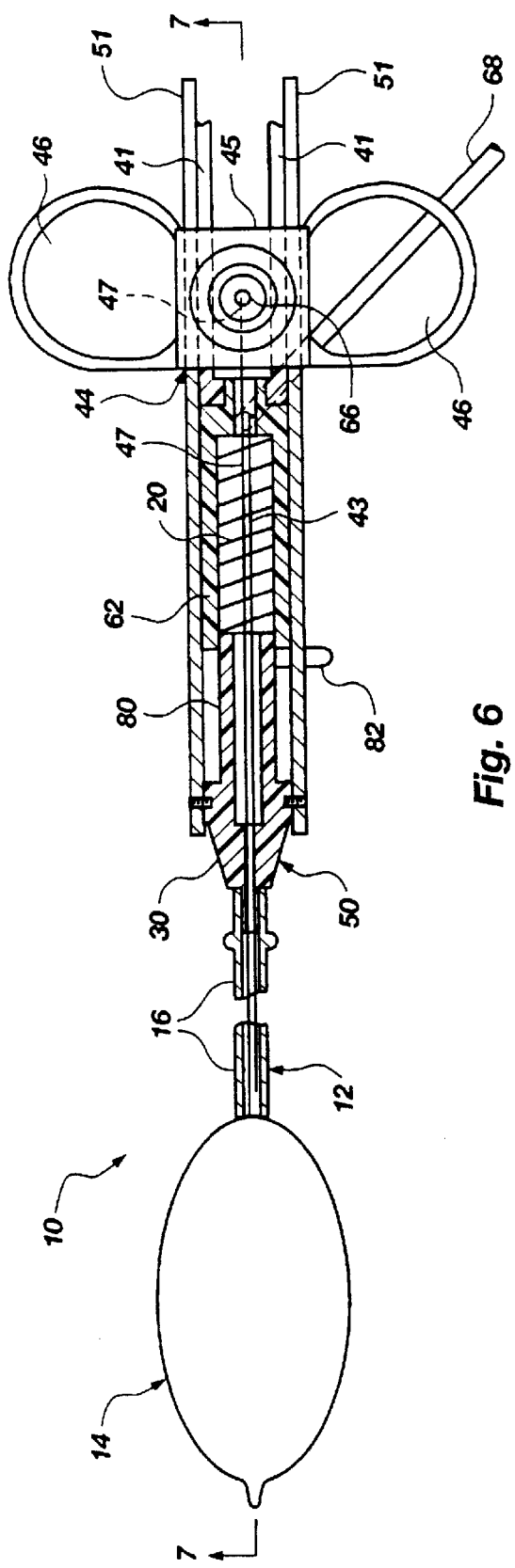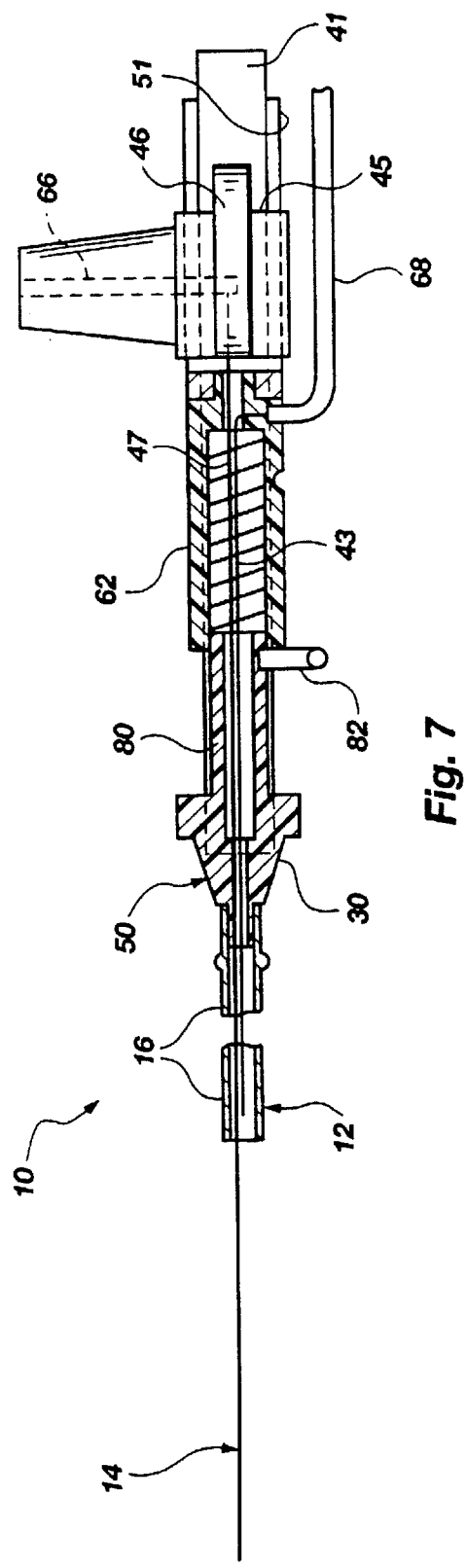
Fig. 6
Fig. 7

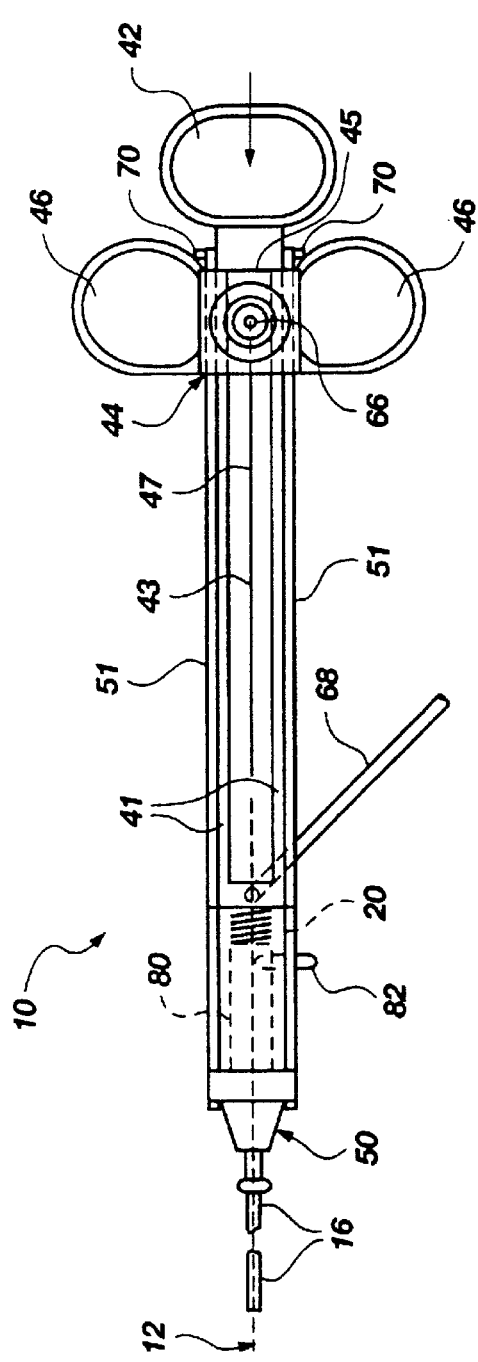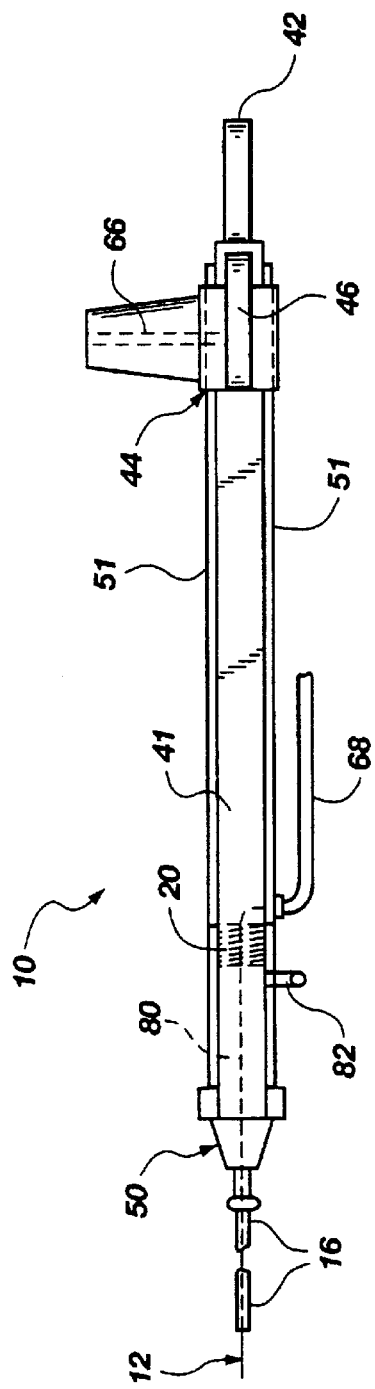
Fig. 8
Fig. 9

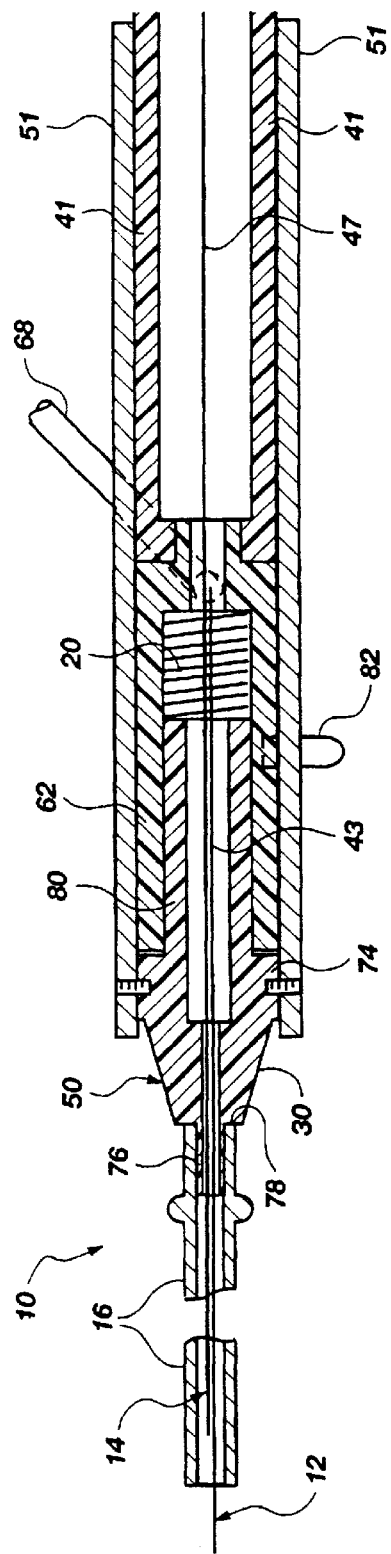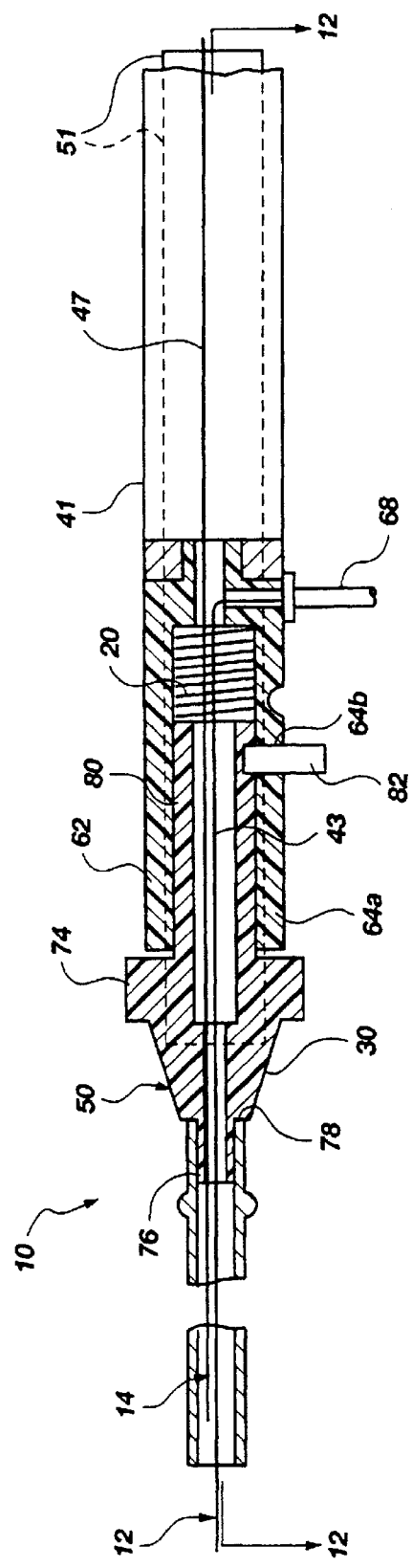
Fig. 12
Fig. 11

SURGICAL COMBINATION APPARATUS HAVING FIRST AND SECOND INSTRUMENTS OPERATED FROM A COMMON ACTUATOR

This application is a continuation of 08/633,958 filed Apr. 15, 1996 now U.S. Pat. No. 5,947,978.

BACKGROUND OF THE INVENTION

The present invention relates to surgical apparatus including a pair of instruments, sheathing means for the instruments and actuating means for extending one or the other instrument from the sheathing means, and more particularly to such apparatus which is a surgical combination inject and snare apparatus.

Commonly owned copending U.S. patent application Ser. No. 08/248,504, filed May 24, 1994, now U.S. Pat. No. 5,542,948, discloses surgical apparatus comprising a first instrument (which may be an injection needle), a second instrument (which may be a snare) and sheathing means (such as a catheter) for sheathing both instruments. Actuator means are provided for simultaneously extending the first instrument relative to the distal end of the sheathing means in a first direction and retracting the second instrument in an opposed second direction relative to the distal end of the sheathing means, and for simultaneously extending the second instrument relative to the distal end of the sheathing means in the first direction and retracting the first instrument in the second direction relative to the distal end of the sheathing means. In other words, the actuator means extends one of the two instruments while simultaneously retracting the other instrument.

The patented apparatus is used by inserting the distal tip thereof into a patient with both the first and second instruments being in an intermediate position, wherein both are covered by the sheathing means. When the distal tip of the sheathing means is properly positioned, the first instrument (typically an injection needle) is extended beyond the sheathing means and into an adjacent polyp. Fluid is then introduced into the polyp causing it to project further inwardly from the wall. At this point the first instrument is withdrawn, and the second instrument (typically a snare) is extended and used to snare the inwardly protruding polyp. This snare may be used simply for physical cutting of the polyp, or it may be electrified to facilitate separation of the polyp from the wall with minimal bleeding. The detached polyp may be withdrawn through the distal tip of the surgical apparatus, or it may be trapped within the interior of the sheathing means to facilitate its withdrawal with the distal tip of the surgical apparatus.

The aforementioned surgical apparatus is susceptible to improvement. For example, in the aforementioned surgical apparatus the force which must be exerted by the surgeon to extend the snare must also include the force required to overcome the friction involved in dragging the injection needle proximately through the sheathing means. A surgeon would be able to manipulate the snare with greater accuracy if he had to exert only the force required to move the snare, and not simultaneously also the force required to move the injection needle.

Further, the surgeon has to manually maintain the injection needle in the extended position during the entire time that it takes to inject sufficient fluid therethrough to cause the polyp to project inwardly from the wall, this step being unnecessarily time-consuming to a surgeon who might have better use for at least one of his hands during this interval if he could lock the needle into an injection position.

Ideally, it should not be necessary for the surgeon to manually retract the injection needle when it is no longer needed, and he should be able to rely on some type of automatic needle retraction mechanism which he could actuate.

The injection needle, like the snare, can be extended a variable and sizable distance distally relative to the distal tip of the sheathing means. However, while it is desirable for the snare to be extendable a variable and sizable distance up to about 5 inches, it is better for the injection needle to be extendable only about 0.75 inch, just sufficient to reach the interior of the polyp. A shorter throw of the needle would also enable a greater curve at the distal end of the sheathing means without danger of the needle becoming caught in the sheathing means (i.e., the catheter) during extending of the needle.

Further, the possibility exists that the injection needle will accidentally be extended when the surgeon's intent is to extend the snare. Thus it would be desirable to have a safety mechanism which had to be disabled in order to enable extension of the needle.

Surgeons acquire great expertise in utilizing hypodermic-type handles (that is, surgical apparatus operated by the first three fingers of a hand), but are typically less familiar with the wheel arrangement of the patented apparatus which must be rotated, say, to withdraw the injection needle and extend the snare.

Accordingly, it is an object of the present invention to provide surgical apparatus, such as a combination inject and snare apparatus, wherein the movement of the first instrument (typically an injection needle) is independent of the movement of the second instrument (typically a snare), thereby to reduce the force which must be exerted during either movement.

Another object is to provide such apparatus which in one embodiment maintains the injection needle in the extended position without further action on the part of the surgeon.

A further object is to provide such surgical apparatus which in one embodiment provides a mechanism for automatic retraction of the needle when it is no longer required.

It is another object to provide such surgical apparatus which in one embodiment incorporates a locking mechanism which must be unlocked in order to enable extension or retraction of the needle.

It is also an object of the present invention to provide such surgical apparatus which in one embodiment enables the snare to be extended a variable and sizeable distance while the injection needle is extendable only a much shorter distance, but typically the full extent of the shorter distance.

SUMMARY OF THE INVENTION

It has now been found the above and related objects of the present invention are obtained in a novel surgical apparatus. The novel surgical apparatus comprises a first instrument (typically, an injection needle), a second instrument (typically, a snare), and sheathing means for sheathing the first and second instruments, the sheathing means having a proximal end and a distal end. An actuator means is provided for manually extending the first instrument a substantially fixed first length (preferably about 0.75 inch) relative to the distal end of the sheathing means and for independently extending or retracting the second instrument a variable second length relative to the distal end of the sheathing means. Biasing means bias the first instrument into retracting relative to the distal end of the sheathing means.

In a preferred embodiment of the surgical apparatus, the actuator means comprises a support assembly, a slider assembly and a rail assembly. The support assembly has a support and means for grasping thereof, the first instrument being secured to the support for movement therewith. The slider assembly has a slider and means for grasping thereof, the slider being secured to the support for sliding movement in opposite directions relative thereto, and the second instrument being secured to the slider for movement therewith. The rail assembly has rail means for enabling independent but non-simultaneous sliding movement of the first instrument in opposite directions relative to the distal end of the sheathing means, the rail means being longitudinally slideable with respect to the support and operatively connected to the slider. Thus, forcible movement of the slider and the rail means to one extreme relative to the support causes the first instrument to extend relative to the distal end of the sheathing means against the biasing means, while release of the slider and the rail means enables the biasing means to return the slider and the rail means from the one extreme, thereby to cause the first instrument to retract. Also, movement of the slider towards the opposite extreme relative to the support causes the second instrument to extend relative to the distal end of the sheathing means.

In a particularly preferred embodiment, movement of the slider towards the one extreme relative to the support causes the second instrument to retract relative to the distal end of the sheathing means. The surgical apparatus additionally includes first automatically engaging and manually disengeable lock means for precluding forcible movement of the slider to the one extreme relative to the support once the biasing means returns the slider from the one extreme, whereby manual disengagement of the lock means is required prior to extension of the first instrument relative to the distal end of the sheathing means. The surgical apparatus additionally includes second automatically engaging and manually disengeable lock means for precluding the biasing means from moving the slider from the one extreme relative to the support after forcible movement of the slider to the one extreme, whereby manual disengagement of the second lock means is required prior to retraction of the first instrument relative to the distal end of the sheathing means.

The present invention also encompasses surgical apparatus comprising a first instrument extendable in a first direction and retractable in a second direction, a second instrument extendable in the first direction and retractable in the second direction, and sheathing means for sheathing the first and second instruments, the sheathing means having a proximal end and a distal end. Means are provided to bias the first instrument in the second direction. A support assembly has a support and means for grasping thereof, the first instrument being secured to the support for movement therewith. A slider assembly has a slider and means for grasping thereof, the slider being secured to the support for sliding movement in opposite directions relative thereto and the second instrument being secured to the slider for movement therewith. A rail assembly has rail means for enabling independent but non-simultaneous sliding movement of the first instrument in opposite directions relative to the distal end of the sheathing means, the rail means being longitudinally slideable with respect to the support and operatively connected to the slider. Thus, forcible movement of the slider and the rail means to one extreme relative to the support causes the first instrument to extend relative to the distal end of the sheathing means against the biasing means, while release of the slider and the rail means enables the biasing means to return the slider and the rail means from the one extreme and the first instrument to retract, and movement of the slider towards the opposite extreme relative to the support causes the second instrument to extend relative to the distal end of the sheathing means.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein:

FIGS. 1 and 2 are fragmentary top plan and side elevational views, respectively, of surgical apparatus according to the present invention, in a "neutral" or "needle in, snare in" orientation;

FIGS. 3, 4, and 5 are fragmentary top plan, side elevational and bottom plan views, respectively, of the surgical apparatus in a "needle in, snare out" orientation;

FIGS. 6 and 7 are fragmentary sectional views thereof, taken along the lines 6—6 of FIG. 4 and 7—7 of FIG. 6, respectively;

FIGS. 8, 9 and 10 are fragmentary top plan, side elevational and bottom plan views, respectively, of the surgical apparatus, in a "needle out, snare in" orientation;

FIGS. 11 and 12 are fragmentary sectional views thereof, taken along the lines 11—11 of FIG. 10 and 12—12 of FIG. 11, respectively.

DETAILED DESCRIPTION OF THE PREFERRED EMBODIMENTS

Figure 13A:
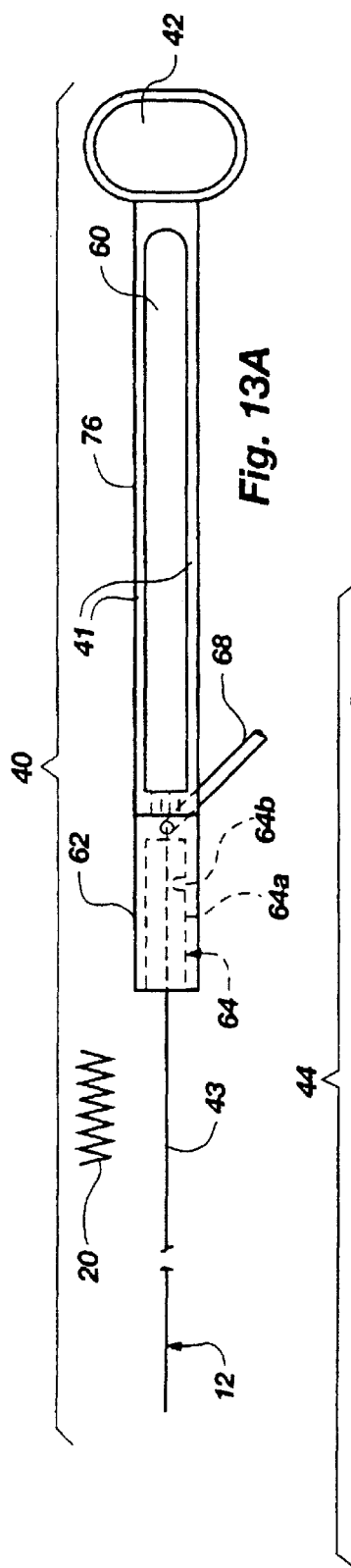
FIGS. 13A, 13B and 13C together form an exploded top plan view thereof separated into independently moveable assemblies.

The improved surgical combination apparatus according to the present invention may incorporate various first and second instruments. While the apparatus shown and described herein is a surgical combination inject and snare apparatus, wherein the first instrument is an injection needle and the second instrument is a snare, those skilled in the surgical arts will readily appreciate that the principles of the present invention have applicability to various other surgical combination apparatus.

Referring now to FIGS. 1 and 2, therein illustrated is a surgical combination apparatus according to the present invention, generally designated by the reference numeral 10. More particularly, the surgical apparatus 10 is a surgical combination inject and snare apparatus including, as a first instrument, a hollow injection needle 12 (best seen in FIGS. 8–12) and, as a second instrument, a snare 14 (best seen in FIGS. 3–7). In addition to the needle 12 and snare 14, the surgical apparatus 10 includes sheathing means 16 for sheathing the first and second instruments 12, 14, actuator means, generally designated 18, for manually controlling movement of the various elements 12, 14 relative to one another, and biasing means 20.

The sheathing means 16 is a conventional catheter, formed of a flexible plastic and defining both an enlarged proximal end 30 fixedly secured to the actuator 18 and a distal or free end 32 for insertion into a patient.

As will become clearer hereinafter, the actuator means 18 includes means for manually extending the first instrument or needle 12 a substantially fixed first length, relative to the distal end 32 of the sheathing means 16, and for independently but non-simultaneously extending or retracting the second instrument or snare 14 a variable second length, relative to the distal end 32 of the sheathing means 16.

The biasing means 20 may be a conventional spring for biasing the first instrument or needle 12 into retracting relative to the distal end 32 of the sheathing means 16.

The actuator means 18 and biasing means 20 together enable the first and second instruments 12, 14 to be both extended and retracted, relative to the distal end 32 of the sheathing means 16.

Turning now in greater detail to the actuator means 18, broadly speaking the actuator means 18 comprises a support assembly generally designated 40, a slider assembly generally designated 44, and a rail assembly generally designated 50.

More particularly, as best seen in FIG. 13A, the axially or longitudinally extending rigid support assembly 40 comprises a support 41 and means 42 for grasping thereof, such as a thumb ring at one end. The first instrument or hollow injection needle 12 is secured to the support 41 by a hollow, flexible wire 43 for movement therewith as a unit. The support 41 at its proximal end, adjacent the grasping means 42, defines an interior longitudinally-extending channel 60 therethrough. The support 41 at its distal end, adjacent the sheathing means 16, defines a hollow cylinder 62 with a closed proximal end and an open distal end. The hollow, flexible wire 43 passes through cylinder 62 and provides fluid communication between needle 12 and hollow tubing 68, the latter being adapted for connection to a fluid source (not shown) and secured to support 41 for movement therewith.

Figure 13B:
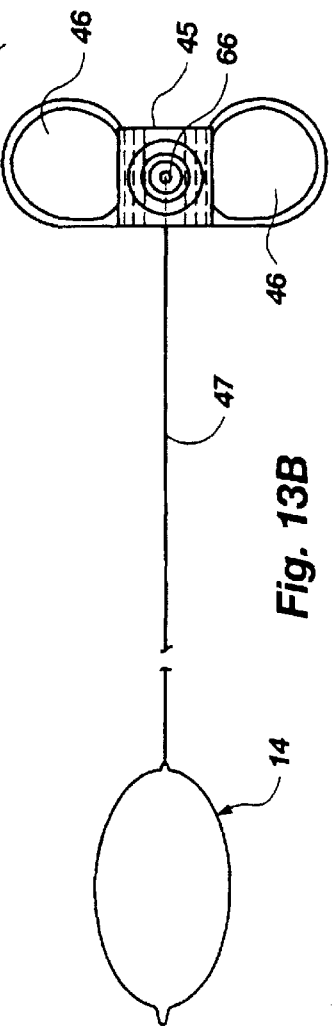

As best seen in FIG. 13B, the slider assembly 44 comprises a slider 45 and means 46 for grasping thereof, such as a pair of finger rings on opposite sides thereof. The slider 45 is secured to the support assembly 40 for sliding longitudinal movement therealong in both directions. The second instrument or snare 14 is secured to the slider 45 by a typically solid, flexible electrically conductive wire 47 for movement therewith as a unit. An electrical contact 66, adapted for conductive communication with a power source (not shown), is secured to slider 45 for movement as a unit therewith and provides for the communication of electrical energy to sheath 14 via conductive wire 47 passing through channel 60 and cylinder 62.

The support 41 and channel 60 of support assembly 40 are configured and dimensioned to receive the slider 45 of slider assembly 44 within the channel 60 and the grasping means 46 of slider assembly 44 laterally outwardly of the support 41, thereby permitting relative movement of the slider 45 and its finger rings 46 relative to the support 41 and its thumb ring 42. As the needle 12 is connected to the support assembly 40 by a flexible wire 43 and the snare 14 is connected to the slider assembly 44 by a flexible wire 47, the needle 12 and snare 14 are in turn capable of relative, albeit non-simultaneous, motion.

Figure 13C:
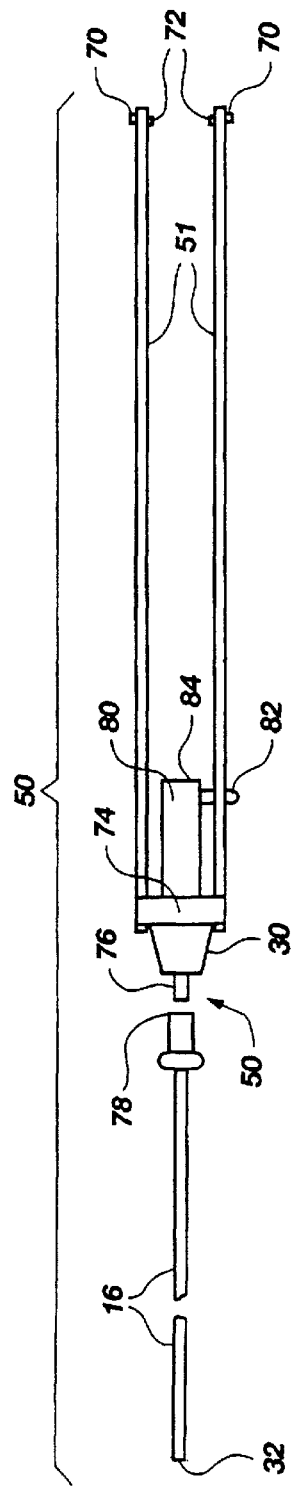

As best seen in FIG. 13C, the axially or longitudinally extending rail assembly 50 is provided for enabling independent but non-simultaneous sliding movement of the first instrument or needle 12 in opposite directions relative to the distal end 32 of the sheathing means 16. The rail assembly 50 includes a pair of parallel rail means 51 longitudinally slidable with respect to the support assembly 40.

The proximal ends of the two rail means 51 each define a small outer lug 70 facing outwardly from the rail means 51 and a small inner lug 72 facing inwardly from the rail means 51 (toward the support 41). The inner lugs 72 are received within longitudinal recesses 75 on the outer surfaces of the rail means 51. The outer lugs 70 act as a stop to limit relative proximal movement of the slider 45 relative to the rail means 51. Accordingly, neglecting any locking means discussed hereinafter, a proximal movement of the slider 45 until it contacts the outer lugs 70 of the rail means 51 results in a retraction of the second instrument or snare 14 relative to the distal end 32 of the sheathing means 16. Further proximal movement of the slider 45 causes a corresponding proximal movement of the rail means 51 along longitudinal recesses 75 (best seen in FIGS. 2 and 4) due to the engagement of the slider 45 and the outer lugs 72, with a resultant exposure of the first instrument or needle 12 distally beyond the distal end 32 of the sheathing means 16.

The distal ends of the two rail means 51 are secured together by a connector 74. The distal end of the connector 74 tapers inwardly and defines a surface 76 adapted to receive the proximal end 78 of catheter 16, such that the entire catheter 16 (including its distal tip 32) moves as a unit with the connector 74 and rail means 51, and thus as a part of the rail assembly 50. Rotatably secured to the proximal end of the connector 74 is a piston 80, which is configured and dimensioned to be slidingly received within the interior of cylinder 62 (along with the spring 20) through the cylinder open distal end. The piston 80 is freely rotatable relative to the connector 74 over at least 45 degrees, but secured to the connector 74 for longitudinal movement as a unit.

It will be appreciated that the support assembly 40 of FIG. 13A, the slider assembly 44 of FIG. 13B and the rail assembly 50 of FIG. 13C are each capable of independent sliding movement relative to one another, thereby to enable the unique motions of the present invention.

Movement of the slider assembly 44 toward the distal extreme relative to the support assembly 40 causes the second instrument or snare 14 to extend relative to the distal end 32 of the sheathing means 16, as illustrated in FIGS. 3–7. Movement of the slider assembly 44 towards the proximal extreme relative to the support assembly 40 causes the second instrument or snare 14 to retract relative to the catheter distal end 32 of the sheathing means 16, as illustrated in the neutral orientation of FIGS. 1–2.

Neglecting for the moment the various locking means provided relative to needle movement, as discussed hereinafter, forcible proximal movement of the slider assembly 44 and the rail assembly 50 to the proximal extreme relative to the support assembly 40 causes the first instrument or needle 12 to extend relative to the distal end 32 of the sheathing means 16 against the biasing means 20, as illustrated in FIGS. 8–12. Release of the slider assembly 44 and rail assembly 50 enables the biasing means 20 to return the slider assembly 44 and rail assembly 50 distally from the proximal extreme, and the first instrument or needle 12 to retract into the sheathing means 16, as illustrated in the neutral orientation of FIGS. 1–2.

Considering now the locking mechanisms, a lever 82 projects radially outwardly from the proximal end of the piston 80 and for rotational and longitudinal travel herewith is configured and dimensioned for travel (with the entire rail assembly 50) along the L-shaped pathway 64 formed within the side wall of cylinder 62. The distal face 84 of piston 80 is at all times disposed within the interior of cylinder 62 (e.g., due to stop pins, not shown) and acts to maintain the spring 20 within the interior of cylinder 62. However, the spring 20 in turn acts to bias the piston 80 for rotation.

Once the lever 82 is manually moved from transverse leg 64b into longitudinal leg 64a, and the rail assembly 50 then moved distally relative to the support assembly 40 (such that lever 82 travels distally along the longitudinal leg 64a and eventually leaves the confines of the longitudinal leg 64a of the L-shaped passageway 64), the spring 20 causes the piston 80 to rotate out of alignment with the longitudinal leg 64a. Because the inner lugs 72 on rail means 51 preferably abut the distal end of the longitudinal recesses 75, lever 82 cannot move distally (and the piston 80 is thus kept at least partially within cylinder 62 even in the absence of the aforementioned stop pins). Because the lever 82 abuts the distal end of the cylinder 62, it cannot move proximally. Thus, longitudinal movement of the lever 82 (and thus the entire rail assembly 50) relative to the cylinder 62 (and thus the entire support assembly 40) is precluded until the lever 82 is manually rotated back into alignment with the longitudinal leg 64a of the L-shaped passageway 64 for distal movement therealong.

Similarly, once the lever 82 has been manually moved from in front of cylinder 62 to within longitudinal leg 64a of the L-shaped passageway 64, and then moved proximally therealong (against the bias of spring 20) until it is aligned with the transverse leg 64b of the L-shaped slot 64, the spring 20 forces the entry of the lever 82 into the transverse leg 64b, thereby to preclude any relative movement longitudinally of the lever 82 (and thus the entire rail assembly 50) relative to the transverse leg 64b (and thus the entire support assembly 40).

Operation of the apparatus is very simple. Referring now to FIGS. 1 and 2, the apparatus 10 is illustrated therein a "neutral" or "needle in, snare in" orientation such as might be used for introduction of the catheter distal tip 32 to the desired location within the patient's body. Neither the needle 12 nor the snare 14 project distally of the catheter distal tip 32 where they might interfere with the threading of the tip 32 through the patient's body. The piston 80 is disposed almost entirely distally of the cylinder 62 with the lever 82 resting on the distal face of the cylinder 62. The proximal end of slider 45 is adjacent to or contacting the outer lugs 70 of the rail means 51.

Referring now to FIGS. 8–12, the apparatus 10 is illustrated therein in the "needle out, snare in" orientation. Once the distal end 32 of catheter 16 has been properly located within the patient, the lever 82 is rotated until it is aligned with the longitudinal leg 64a of the L-shaped passageway 64 of cylinder 62. At the same time the finger grips 46 and thumb grip 42 are used to move the slider 45 proximally first against the outer lugs 70 of the rail means 51 and then even further proximally until the rail means 51 (and thus the entire rail assembly 50) moves proximally. The inner lugs 72 of the rail means 51 (best seen in FIG. 13C) slidingly travel distally within the longitudinal recesses 75 on the outer surfaces of the support 41 (best seen in FIGS. 2 and 4). At this point, as best seen in the FIGS. 8 and 9, the finger grips 46 are closely disposed relative to the thumb grip 42.

During the above-described movement of the rail means 51 proximally relative to the support 41, the lever 82 travels along the longitudinal leg 64a and the piston 80 progressively enters the hollow cylinder 62. Finally, the lever 82 becomes aligned with the transverse leg 64b and, under the influence of spring 20, moves along the transverse leg 64b, thereby blocking any further longitudinal movement of the rail assembly 50 relative to the support assembly 40. Typically, although not necessarily, there is still room within the longitudinal recesses 75 for further proximal movement of the rail assembly 50 relative to the support assembly 40 as the relative motion therebetween is best precluded by the interaction of the lever 82 and passageway 64 in order to achieve a locking effect. The length of longitudinal leg 64a is preferably about 0.75 inch, although it may be shorter or longer depending upon the desired travel of the first instrument 12.

Depending upon what one uses as the point of reference, in the "needle out, snare in" orientation, either the distal movement of the support assembly 40 relative to the rail assembly 50 results in a distal movement of the needle 12 relative to the catheter 16 or the distal movement of the rail assembly 50 relative to the support assembly 40 causes the catheter 16 to move proximally relative to the needle 12 such that the catheter distal tip 32 now exposes the distal tip of the needle 12. In actuality, typically the catheter distal tip 32 is initially set against the polyp by the surgeon and the movement to the "needle out, snare in" orientation is effected by a forward movement of the support assembly 40 relative to the rail assembly 50. The forward motion is driven and controlled by the thumb movement in thumb ring 42, but it must first be enabled by the manual pivoting of lever 82 into alignment with the longitudinal leg 64a (i.e., unlocking of lever 82). In any case, it will be appreciated that once the lever 82 has traversed the length of the longitudinal leg 64a, and then entered into the transverse leg 64b (under the influence of spring 20), the apparatus is locked in the "needle out, snare in" orientation. At this time, the desired fluid may be introduced into the polyp through hollow tubing 68, hollow wire 43, and needle 12 without further action on the part of the surgeon to maintain the injection needle 12 in place. On the other hand, it should also be appreciated that the lever 82 initially acted as a safety or locking mechanism, precluding any distal advancement of the needle 12 until the lever 82 was manually aligned with the longitudinal leg 64a.

After sufficient fluid has been introduced into the polyp through hollow tubing 68, wire 43, and injection needle 12, the fluid flow is terminated. Then the lever 82 need only be back rotated along transverse leg 64b until it is again in alignment with longitudinal leg 64a (i.e., again unlocked). At this point the energy stored in the compressed spring 20 will force piston 80 almost entirely out of the cylinder 62 and cause the piston 80 to rotate until lever 82 returns to its normal locked position outside of the passageway 64. Further forward movement of the rail assembly 50 relative to the support assembly 40 is precluded by the abutment of the inner lugs 72 on the distal ends of the recesses. Due to the biasing of spring 20, it is almost impossible to manually maintain piston 80 in an intermediate position within cylinder 62—i.e., with the lever 82 in the middle of longitudinal leg 64a—so that the needle/piston travel is typically for the full length of longitudinal leg 64a. Thus, the surgeon has only to release the thumb pressure exerted on thumb grip 42 and rotate lever 82 within the transverse leg 64b; thereafter, the apparatus automatically returns itself, under the influence of spring 20, to the "neutral" orientation illustrated in FIGS. 1 and 2.

Referring now to FIGS. 3–7, the apparatus 10 is illustrated therein in the "needle in, snare out" orientation. Once the polyp has been injected with fluid from the injection needle 12, the latter is returned to the neutral orientation. From there, the surgeon has only to move the slider assembly 44 distally relative to the rail assembly 50. This is easily accomplished by separating the fingers in the finger grips 46 from the thumb in the thumb grip 42. The abutment of the distal end of the slider 45 against the distal end of the channel 60 limits the forward movement of the slider 45 (and hence the slider assembly 44) relative to the now locked together supra-assembly formed by the support assembly 40 and the rail assembly 50. It will be appreciated that the piston 80 and lever 82 and the cylinder 62 and passageway 64 play no role in the movement of the sheath 14 relative to the catheter distal end 32.

The surgeon has only to manipulate reciprocatingly the finger grips 46 relative to the thumb grip 42 in order to cause distal emergence of the sheath 14, trapping of the protruding polyp thereby, and withdrawal of the sheath 14 (either with or without the polyp) back into the catheter 16. Electrical energy may be introduced into the sheath 14 via contact 66 and electrically conductive wire 47.

To summarize, in the present invention the movement of the injection needle 12 is independent of the movement of the snare 14, thereby to reduce the force which must be exerted during either movement. The interaction of the lever 82 and the passageway 64 provides a locking mechanism which must be manually unlocked in order to enable either extension or retraction of the needle, which enables the injection needle 12 to be maintained in the extended position without further action on the part of the surgeon, and which provides automatic retraction of the needle 12 when it is no longer required. The preferred embodiment allows the snare 14 to be extended a variable and sizable distance, limited essentially only by the length of channel 60, while the injection needle 12 is extendable only a much shorter distance, typically limited by the length of the longitudinal leg 64a. Typically the extension of the needle 12 is for the full extent of the short distance as the maintenance of the lever 82 within the longitudinal leg 64a is unstable due to the biasing of spring 20.

Now that the preferred embodiments of the present invention have been shown and described, various modifications and improvements thereon will become readily apparent to those skilled in art. Accordingly, the spirit and scope of the present invention is to be construed broadly and limited only by the following claims, and not by the foregoing specification.

I claim:

1. A surgical apparatus, comprising:
   (A) a needle;
   (B) a snare;
   (C) sheathing means for sheathing said needle and snare, said sheathing means having a proximal end and a distal end;
   (D) actuator means for extending said needle a substantially fixed first length relative to said distal end of said sheathing means, and for independently extending or retracting said snare a variable second length relative to said distal end of said sheathing means, the needle and snare being extendible and retractable independently from each other, thereby facilitating free movement of the needle and snare relative to each other; and
   (E) biasing means biasing said first instrument into retracting relative to said distal end of said sheathing means.

2. The surgical apparatus of claim 1, wherein said actuator means comprises:
   (A) a support having means for grasping thereof, said first instrument being secured to said support for movement therewith;
   (B) a slider having means for grasping thereof, said slider being secured to said support for sliding movement in opposite directions relative thereto, and said second instrument being secured to said slider for movement therewith;
   (C) rail means for enabling independent but non-simultaneous sliding movement of said first instrument in said opposite directions relative to said distal end of said sheathing means, said rail means being longitudinally slideable with respect to said support and operatively connected to said slider;
   whereby forcible movement of said slider and said rail means to one extreme relative to said support causes said first instrument to extend relative to said distal end of said sheathing means against said biasing means, while release of said slider and said rail means enables said biasing means to return said slider and said rail means from said one extreme and said first instrument to retract; and
   whereby movement of said slider towards the opposite extreme relative to said support causes said second instrument to extend relative to said distal end of said sheathing means.

3. The surgical apparatus of claim 2 wherein movement of said slider towards said one extreme relative to said support causes said second instrument to retract relative to said distal end of said sheathing means.

4. The surgical apparatus of claim 3 additionally including first automatically engaging and manually disengeable lock means for precluding forcible movement of said slider to said one extreme relative to said support once said biasing means returns said slider from said one extreme, whereby manual disengagement of said lock means is required prior to extension of said first instrument relative to said distal end of said sheathing means.

5. The surgical apparatus of claim 4 additionally including second automatically engaging and manually disengeable lock means for precluding said biasing means from moving said slider from said one extreme relative to said support after forcible movement of said slider to said one extreme, whereby manual disengagement of said second lock means is required prior to retraction of said first instrument relative to said distal end of said sheathing means.

6. The surgical apparatus of claim 1, wherein said fixed first length is about 0.75 inch.

7. A surgical apparatus, comprising:
   (A) a needle attached to an elongated extension line for communicating fluids to and from said needle, said needle being extendable in a first direction and retractable in a second direction;
   (B) a snare attached to an elongated extension line and extendable in said first direction and retractable in said second direction;
   (C) sheathing means for sheathing said needle, said snare and said extension lines, said sheathing means having a proximal end and a distal end;
   (D) actuator means for extending said needle in said first direction and for independently extending and retracting said snare in said first and second directions, respectively, relative to said distal end of said sheathing means, the needle and snare being extendible and retractable independently from each other, thereby facilitating free movement of the needle and snare relative to each other during retraction of the needle; and
   (E) means biasing said needle in said second direction relative to said distal end of said sheathing means.

8. The surgical apparatus of claim 7, wherein said actuator means comprises:
   (A) a support having means for grasping thereof, said needle being secured to said support for movement therewith;

(B) a slider having means for grasping thereof, said slider being secured to said support for sliding movement in said first direction and said second direction relative thereto, and said snare being secured to said slider for movement therewith; and (C) rail means for enabling independent but non-simultaneous sliding movement of said needle relative to said distal end of said sheathing means in opposite directions, said rail means being longitudinally slidable with respect to said support and operatively connected to said slider;

whereby forcible movement of said slider and said rail means to one extreme relative to said support causes said needle to extend relative to said distal end of said sheathing means against said biasing means, while release of said slider and said rail means enables said biasing means to return said slider and said rail means from said one extreme and said needle to retract; and whereby movement of said slider towards the opposite extreme relative to said support causes said snare to extend relative to said distal end of said sheathing means.

9. The surgical apparatus of claim 8 wherein movement of said slider towards said one extreme relative to said support causes said snare to retract relative to said distal end of said sheathing means.

10. The surgical apparatus of claim 9 additionally including first automatically engaging and manually disengeable lock means for precluding forcible movement of said slider to said one extreme relative to said support once said biasing means returns said slider from said one extreme, whereby manual disengagement of said lock means is required prior to extension of said needle relative to said distal end of said sheathing means.

11. The surgical apparatus of claim 10 additionally including second automatically engaging and manually disengeable lock means for precluding said biasing means from moving said slider from said one extreme relative to said support after forcible movement of said slider to said one extreme, whereby manual disengagement of said second lock means is required prior to retraction of said needle relative to said distal end of said sheathing means.

12. A surgical apparatus, comprising:

(A) a first instrument extendable in a first direction and retractable in a second direction;

(B) a second instrument extendable in said first direction and retractable in said second direction;

(C) sheathing means for sheathing said first and second instruments, said sheathing means having a proximal end and a distal end;

(D) means biasing said first instrument in said second direction;

(E) a support having means for grasping thereof, said first instrument being secured to said support for movement therewith;

(F) a slider having means for grasping thereof, said slider being secured to said support for sliding movement in opposite directions relative thereto and said second instrument being secured to said slider for movement therewith; and (G) rail means for enabling independent but non-simultaneous sliding movement of said first instrument in said opposite directions relative to said distal end of said sheathing means, said rail means being longitudinally slideable with respect to said support and operatively connected to said slider;

whereby forcible movement of said slider and said rail means to one extreme relative to said support causes said first instrument to extend relative to said distal end of said sheathing means against said biasing means, while release of said slider and said rail means enables said biasing means to return said slider and said rail means from said one extreme and said first instrument to retract; and whereby movement of said slider towards the opposite extreme relative to said support causes said second instrument to extend relative to said distal end of said sheathing means.

13. The surgical apparatus of claim 12 wherein movement of said slider towards said one extreme relative to said support causes said second instrument to retract relative to said distal end of said sheathing means.

14. The surgical apparatus of claim 12 additionally including first automatically engaging and manually disengeable lock means for precluding forcible movement of said slider to said one extreme relative to said support means once said biasing means returns said slider from said one extreme, whereby manual disengagement of said lock means is required prior to extension of said first instrument relative to said distal end of said sheathing means; and second automatically engaging and manually disengeable lock means for precluding said biasing means from moving said slider from said one extreme relative to said support means after forcible movement of said slider to said one extreme, whereby manual disengagement of said second lock means is required prior to retraction of said first instrument relative to said distal end of said sheathing means.

15. The surgical apparatus of claim 12, wherein said first instrument comprises an injection needle and said second instrument comprises a snare.

* * * * *